United States Patent [19]

Wuts

[11] Patent Number: 5,175,298

[45] Date of Patent: Dec. 29, 1992

[54] DIPEPTIDE HYDROXY ETHYLENE ISOSTERE SYNTHESIS AND INTERMEDIATES THEREFOR

[75] Inventor: Peter G. M. Wuts, Galesburg, Mich.

[73] Assignee: The Upjohn Company, Kalamazoo, Mich.

[21] Appl. No.: 623,702

[22] PCT Filed: Jun. 8, 1989

[86] PCT No.: PCT/US89/02452

§ 371 Date: Dec. 11, 1990

§ 102(e) Date: Dec. 11, 1990

Related U.S. Application Data

[63] Continuation of Ser. No. 213,787, Jun. 30, 1988, abandoned.

[51] Int. Cl.$^5$ ............................................. C07D 263/26
[52] U.S. Cl. ................................... 548/230; 549/477; 549/478; 544/238; 544/369; 544/139; 548/217
[58] Field of Search ........................................... 548/230

[56] References Cited

U.S. PATENT DOCUMENTS

| | | | |
|---|---|---|---|
| 4,150,020 | 4/1979 | Singh | 548/230 |
| 4,479,005 | 10/1984 | Kleschick | 548/230 |
| 4,880,781 | 11/1989 | Hester et al. | 530/331 |
| 4,940,797 | 7/1990 | Jones | 548/230 |
| 5,012,000 | 4/1991 | Illig | 548/230 |

FOREIGN PATENT DOCUMENTS 0173481 3/1986 European Pat. Off. .
90-00166 1/1990 PCT Int'l Appl. ................ 548/230

OTHER PUBLICATIONS

Kleschick et al., J. Org. Chem. vol. 52 pp. 3168-3169 (1987).
Evans (IV) Aldrichimica Acta vol. 15 No. 2 pp. 23-31 (1982).
Evans (I) Jour. Am. Chem. Soc. 1982 (vol. 104) pp. 1737-1739.
Evans (II) Jour. Am. Chem Soc. 1985 (vol. 107) pp. 4346-4348.
Evans (III) Chem. Abstr. vol. 102 Entry 148504U.
Block, Chem. Abstr vol. 109 Entry 170091S.
Herold et al., Jour Org. Chem. vol. 54 (No. 5) pp. 1179-1185 (1989).
Evans et al. (V) Chem Abstr vol. 108 Entry 150929(X) (1987).
Evans et al., Tetrahedron Letters vol. 23 pp. 4577-4580 (1982).
Baker et al. Jour. Chem. Soc, Chem. Commun. 1986, pp. 874-876.

Primary Examiner—Donald G. Daus
Attorney, Agent, or Firm—Lawrence T. Welch

[57] ABSTRACT

The present invention provides processes and intermediates for one preparation of the hydroxy ethylene isostere dipeptide of leu-val which is itself useful in the preparation of renin inhibitory peptides. The process employs certain novel oxazolidenes.

1 Claim, No Drawings

DIPEPTIDE HYDROXY ETHYLENE ISOSTERE SYNTHESIS AND INTERMEDIATES THEREFOR

This application is the national phase of international application PCT/US89/02452, filed Jun. 8, 1989, which designated the U.S.; which is a continuation of U.S. application Ser. No. 07/213,787, filed Jun. 30, 1988, now abandoned.

BACKGROUND OF THE INVENTION

The present invention provides novel processes and intermediates for the synthesis of the hydroxyethylene isostere dipeptide leu-val and similar transition state moieties. These compounds are useful in the synthesis of a large number of renin inhibitory peptides having this moiety in the 10,11 position corresponding to the renin substrate. See, e.g., U.S. Pat. No. 4,880,781, which is incorporated by reference herein. The sequence may readily be modified for the preparation of a large variety of both the N-terminal and C-terminal variants. When hydroxy ethylene isosteres of this type are incorporated into a variety of peptides they have enhanced or altered biological activity which makes them useful for treatment of a variety of disease states, particularly the treatment of hypertension.

INFORMATION DISCLOSURE

The use of the hydroxyethylene isostere dipeptide leu-val to prepare renin inhibitors is known. D. Tourwe, Janssen Chim. Acta, 3, (1985) gives a very brief review of some of the earlier work on transistion state analogs of dipeptides. This review gives the background and utility of dipeptide isosteres.

M. W. Holladay, et al., J. Med. Chem., 30, 375 (1987) describes the synthesis of Leu-gly and Leu-ala dipeptide isosteres and gives some biological data on their effectiveness as inhibitors when incorporated into renin inhibitory peptides.

M. W. Holladay, et al., Tetrahedron Letters, 24 (1983) describes the synthesis of the Leu-ala dipeptide isostere.

B. E. Evans, et al., J. Org. Chem., 50, 4615 (1985) describes a synthesis of the Phe-Phe dipeptide isostere.

D. J. Kempf, J. Org. Chem., 51, 3921 (1986) describes the preparation of the following dipeptide isosteres: Phe-ala, Phe-(BnS)ala, Phe-leu, Phe-(allyl)ala and Phe-phe.

A. H. Fray, et al., J. Org. Chem., 51, 4828 (1986) describes the thesis of the dipeptide hydroxyethylene isosteres Leu-leu, leu-gly and Leu-(2-propenyl)ala.

U.S. Pat. No. 4,613,676 describes an in situ preparation of Leu-val hydroxyethylene dipeptide isostere.

M. Szelke, et al., (1983) Novel Transition State Analogs of Renin. In V. J. Hruby and D. H. Rich (Eds.), Peptides: Structure and Function, Pierce Chem. Co., Rockford, Ill., pp 583–586, describes a synthesis of the hydroxyethylene isostere, Leu-val.

European patent application 173,481, published on Mar. 5, 1986, discloses the incorporation of Leu-val in renin inhibitory peptides.

SUMMARY OF THE INVENTION

The present invention particularly provides:
(1) A compound of the formula I wherein $R_1$ and $R_2$ are the same or different and are
 (a) $C_1$–$C_{10}$alkyl,
 (b) $C_2$–$C_{10}$alkenyl,
 (c) aryl,
 (d) $C_1$–$C_{10}$alkoxy,
 (e) $C_1$–$C_{10}$alkylthio,
 (f) Het, or
 (g) —O—$CH_2$-aryl;
wherein $R_3$ is
 (a) $C_1$–$C_{10}$alkyl,
 (b) benzyl, or
 (c) substituted benzyl;
wherein $R_4$ is
 (a) hydrogen,
 (b) $C_1$–$C_{10}$alkyl, or
 (c) aryl;
wherein $R_5$ is
 (a) hydrogen,
 (b) $C_1$–$C_{10}$alkyl, or
 (c) $C_2$–$C_{10}$alkenyl;
wherein aryl is phenyl or naphthyl substituted by zero to 3 of the following:
 (a) $C_1$–$C_{10}$alkyl,
 (b) hydroxy,
 (c) $C_1$–$C_{10}$alkoxy,
 (d) halo, or
 (e) $C_1$–$C_{10}$alkylthio, or
 (f) Het;
wherein -Het is a 5- or 6-membered saturated or unsaturated ring containing from one to three heteroatoms selected from the group consisting of nitrogen, oxygen, and sulfur; and including any bicyclic group in which any of the above heterocyclic rings is fused to a benzene ring, which heterocyclic moiety is substituted with zero to three of the following:
 (i) $C_1$–$C_6$alkyl,
 (ii) hydroxy,
 (iii) trifluoromethyl,
 (iv) $C_1$–$C_4$alkoxy,
 (v) halo,
 (vi) aryl,
 (vii) aryl $C_1$–$C_4$alkyl-,
 (viii) amino, and
 (ix) mono- or di-($C_1$–$C_4$alkyl)amino; and
(2) A compound of the formula II wherein $R_7$ is
 (a) $C_1$–$C_{10}$alkyl, or
 (b) —$CH_2$-aryl;
wherein $R_8$ is
 (a) hydroxy,
 (b) —$N_3$,
 (c) —$NH_2$,
 (d) —NH—C(O)—O—$R_{10}$, or
 (e) —O—$SO_2R_{11}$;
wherein $R_9$ is
 (a) $C_1$–$C_{10}$alkyl, or
 (b) ($C_1$–$C_4$alkyl)-aryl;
wherein $R_{10}$ is
 (a) tert-butyl,
 (b) benzyl,
 (c) $C(CO_3)CH_2$—,
 (d) methyoxy benzyl, or
 (e) fluorenyl;
wherein $R_{11}$ is
 (a) $C_1$–$C_{10}$alkyl,
 (b) ($C_1$–$C_4$alkyl)aryl, or
 (c) $C_nF_{n+1}$;
wherein n is 1 to 5;
wherein aryl is phenyl or naphthyl substituted by zero to 3 of the following:
 (a) $C_1$–$C_{10}$alkyl,
 (b) hydroxy, (c) $C_1$-$C_{10}$alkoxy,
(d) halo, or
(e) $C_1$-$C_{10}$alkylthio, or
(f) Het;

wherein -Het is a 5- or 6-membered saturated or unsaturated ring containing from one to three heteroatoms selected from the group consisting of nitrogen, oxygen, and sulfur; and including any bicyclic group in which any of the above heterocyclic rings is fused to a benzene ring, which heterocyclic moiety is substituted with zero to three of the following:

(i) $C_1$-$C_6$alkyl,
(ii) hydroxy,
(iii) trifluoromethyl,
(iv) $C_1$-$C_4$alkoxy,
(v) halo,
(vi) aryl,
(vii) aryl $C_1$-$C_4$alkyl-,
(viii) amino, and
(ix) mono- or di-($C_1$-$C_4$alkyl)amino.

Surprisingly and unexpectedly the present invention provides an efficient and stereospecific means to prepare intermediates for renin inhibitory peptides.

The carbon atom content of various hydrocarbon-containing moieties is indicated by a prefix designating the minimum and maximum number of carbon atoms in the moiety, i.e., the prefix ($C_i$-$C_j$) indicates a moiety of the integer "i" to the integer "j" carbon atoms, inclusive. Thus ($C_1$-$C_{10}$)alkyl refers to alkyl of one to 4 carbon atoms, inclusive, or methyl, ethyl, propyl, butyl, pentyl, hexyl, octyl, nonyl, decyl and isomeric (cyclic, acylic, branched) forms thereof.

Examples of aryl include phenyl, naphthyl, (o-, m-, p-)tolyl, (o-, m-, p-)ethylphenyl, 2-ethyl-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylpyhenyl, (2,3,4- 2,3,6-, or 2,4,5-)trimethylphenyl, (o-, m-, or p-)fluorophenyl, (o-, m-, or p-trifluoromethyl)phenyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5- or 6-)chloro-o-tolyl, 4-chloro-2-propylphenyl, 2-isopropyl-4-chlorophenyl, 4-chloro-3-fluorophenyl, (3- or 4-)chloro-2-fluorophenyl, (o-, m-, or p-)trifluoromethylphenyl, (o-, m-, or p-)ethoxyphenyl, (4- or 5-)chloro-2-methoxyphenyl, and 2,4-dichloro(5- or 6-)methylphenyl.

Examples of -Het include: 2-, 3-, or 4-pyridyl, imidazolyl, indolyl, $N^{in}$-formyl-indolyl, $N^{in}$-$C_2$-$C_5$alkyl-C(O)-indolyl, [1,2,4]-triazolyl, 2-, 4-, 5-pyrimidinyl, 2-, 3-thienyl, piperidinyl, pyrryl, pyrrolinyl, pyrrolidinyl, pyrazolyl, pyrazolinyl, pyrazolidinyl, imidazolinyl, imidazolidinyl, pyrazinyl, piperazinyl, pyridazinyl, oxazolyl, oxazolidinyl, isoxazolyl, isoxazolidinyl, morpholinyl, thiazolyl, thiazolidinyl, isothiazolyl, isothiazolidinyl, quinolinyl, isoquinolinyl, benzimidazolyl, benzothiazolyl, benzoxazolyl, furyl, thienyl, and benzothienyl. Each of these moieties may be substituted as noted above.

As is apparent to those of ordinary skill in the art, the intermediates herein and inhibitory peptides prepared therefrom can occur in several isomeric forms, depending on the configuration around the asymmetric carbon atoms. All such isomeric forms are included within the scope of the present invention. Preferably, the stereochemistry of the amino acids corresponds to that of the naturally-occurring amino acids.

As would be generally recognized by those skilled in the art of organic chemistry, a heterocycle as defined herein for -Het would not be bonded through oxygen or sulfur or through nitrogen which is within a ring and part of a double bond.

The hydroxyethylene isostere dipeptides prepared herein are incorporated into renin-inhibitory peptides by conventional means.

Generally, the renin inhibiting polypeptides may be prepared by either polymer assisted or solution phase peptide synthetic procedures analogous to those described hereinafter or to those methods known in the art. For example, the carboxylic moiety of $N^{\alpha}$-t-butyloxycarbonyl (Boc)-substituted amino acid derivatives having suitable side chain protecting groups, if necessary, may be condensed with the amino functionality of a suitably protected amino acid, peptide or polymer-bound peptide using a conventional coupling protocol such as dicyclohexylcarbodiimide (DCC) and 1-hydroxybenzotriazole (HOBT) or diethylphosphoryl cyanide (DEPC) and triethylamine ($Et_3N$) in methylene chloride or dimethylformamide. The synthetic procedures used to incorporate the novel moieties herein are analogous to those described, for example, in U.S. Pat. Nos. 4,424,207; 4,470,971; 4,477,440; 4,477,441; 4,478,826; 4,478,827; 4,479,941; and 4,485,099, and copending application Ser. No. 753,198, filed Jul. 9, 1985, and copending application Ser. No. 825,250, filed Feb. 3, 1986, all of which are expressly incorporated by reference herein. See, also, published European patent applications 45,161; 45,665; 53,017; 77,028; 77,029; 81,783; 104,041; 111,266; 114,993; and 118,223.

The compounds and processes of this invention are depicted in Chart A and as described below. As would be apparent to one of ordinary skill in the art, analogous procedures can be used to prepare the remaining compounds of this invention.

DESCRIPTION OF THE PREFERRED EMBODIMENTS

Preparation of Compound 4 Compound 3 is prepared from isopropyloxazolidinone, butyllithium and isovaleryl chloride according to Evans (see Aldrichimica Acta, 15:23 (1982). A solution of LDA (Lithium diisopropylamide) in THF (tetrahydrofuran) is prepared from 0.25 ml of diisopropyl amine and n-butyllithium (1.6M) at $-78°$ C. To this solution is added imide 3 in THF. After 40 min., bromide 2 is added and the reaction is warmed to $-30°$ C. after stirring at $-78°$ for 1.5 h. The mixture is placed in the freezer overnight after stirring at $-30°$ for 3 hours. The mixture is poured into water and isolated with MTBE (Methyl t-butyl ether) to afford the crude adduct 4.

Other amide bases such as $KN(TMS)_2$ (potassium hexamethyldisilazide) and $NaN(TMS)_2$ (sodium hexamethyldisilazide) also work in the reaction. The preferred temperature range is between $-30°$ and $-20°$ C. Lower temperatures stall the reaction and higher temperatures cause decomposition of the enolate through its ketene. The optimum time has also not been established.

Preparation Compounds 5 and 6 A mixture of imide 4 in methylene chloride is cooled to $0°$ C. and treated with m-chloroperoxybenzoic acid (80% pure). The mixture is stirred overnight and allowed to slowly warm to room temperature. The product is isolated by extraction with MTBE from 10% KOH. The organic extracts are dried over magnesium sulfate and concentrated to afford the epoxides 5 and 6 as a viscous oil.

Other peracids such as trifluoroperoxyacetic, peroxyacetic, perphathalic acid and magnesium perphthalate also work in this reaction. Again temperature merely changes the rate of the reaction. Other solvents such as toluene, dichloroethane, butyl chloride will also work.

Preparation of Compounds 7 and 8 The epoxide hydrolysis and lactonization to form hydroxy lactones 7 and 8 is undertaken as follows.

The crude mixture of epoxides 5 and 6 from above is taken up in THF and 10% sulfuric acid and heated to reflux overnight. The product is isolated with MTBE and chromatographed on silica gel with 25% ethyl acetate/cyclohexane to afford the lactones as a mixture of the (2S, 4R, 5S)-isomer and the (2S, 4S, 5R)-isomer in a ratio of 56:40 as determined by capillary GC. Retention times are 4.52 and 4.72, respectively, 150° C. 15 meter column.

The mixture of lactones 7 and 8 (ratio ≈4:1, minor isomer is desired) is dissolved in methylene chloride, cooled to −10° C. and treated with triethylamine. The mixture is cooled to −16° C. and methanesulfonyl chloride (22.8 g, 0.20 mol) is added over a 2 h period. When TLC shows the reaction to be complete, the mixture is washed with 5% sodium bicarbonate (NaHCO$_3$), dried over sodium sulfate (NaSO$_4$) and concentrated under reduced pressure to afford an oil. The NMR spectrum shows the mesylate methyl at 3.2 ppm. If desired, the mesylates are separated by silica gel chromatography with 15% ethyl acetate/hexane.

Other leaving groups such as tosylate and trifluoromethane sulfonate should also be effective in this reaction. Any tertiary amine may serve as a suitable acid scavenger.

Inversion of lactone mixture: The crude mesylate mixture from above is dissolved in acetonitrile in a 1 l flask equipped with mechanical stirrer, thermometer and nitrogen inlet. To this solution is added a solution of potassium hydroxide (KOH) in water. The resulting mixture is stirred at room temperature overnight. The mixture is acidified with 10% HCl to pH 1 and extracted with ethyl acetate. The organic layers are dried over Na$_2$SO$_4$ and concentrated to afford the inverted lactones 7 and 8 as a 21.6:70.9 mixture of the (2S, 4R, 5S)-isomer to the (2S, 4S, 5R)-isomer. The NMR spectrum shows very little difference from the original lactone mixture.

Leaving groups such as tosylate, trifluoromethanesulfonate should be just as effective in the inversion reaction. NaOH will also work. It does not matter what acid is used to acidify the mixture. The ratio of isomers varies somewhat, but, in general, it comes out the reverse of what went in.

Compounds 9a and 9b are prepared as follows: The lactone mixture from above is dissolved in methylene chloride and treated with triethylamine. The solution is cooled to −10° C. and slowly treated with methanesulfonyl chloride over a 1 h period. The reaction mixture is stirred for 0.5 h and then washed with sodium bicarbonate, dried over sodium sulfate and concentrated to afford an oil. The NMR shows the mesylate protons at 3.05 ppm.

Preparation of Compounds 10a and 10a The crude mesylate from above is dissolved in DMSO and treated with 59.9 g of PEG-300, and 43.2 g of sodium azide. The mixture is heated to 70° C. overnight under a nitrogen atmosphere, cooled to room temperature and poured into 250 ml of half saturated brine and 250 ml of ethyl acetate. The organic layers are washed with one-half saturated brine, dried over sodium sulfate and concentrated to afford the azides 10a and 10b.

Other solvents which are useful in this reaction include DMF, dimethylacetamide and N-methylpyrolidone. The reaction will work without the PEG-300 but will be somewhat slower. Temperatures beyond 70° should work although a yield loss might be encountered. Lower temperatures will slow down the reaction.

Amines 11a and 11b: A solution of the azides 10a and 10b in absolute ethanol and 10% Pd/C is hydrogenated at 28 psi for 4 hours. The catalyst is removed by filtration through solka flock and the filtrate is concentrated to a viscous oil which is not characterized further. TLC in 25% ethyl acetate/hexane shows a red (characteristic of primary amine) origin spot when developed in ninhydrin.

The reduction may be performed with a variety of catalysts such as Pt and Ni or by chemical means such as vanadous chloride, sodium hydrosulfite, aluminum amalgam, titanium trichloride, hydrogen sulfide and 1,3-propanedithiol.

Preparation of Compounds 1a and 1b T-butoxycarbonyl (T-Boc) amino lactones 1a and 1b are prepared as follows: The crude oil from above is taken up in THF and saturated sodium bicarbonate and T-Boc anhydride. The mixture is stirred at room temperature overnight. Extraction with ethyl acetate from water affords a mixture of lactones 1a and 1b. Crystallization from 1:1 ethyl acetate/heptane affords the pure (2S, 4S, 5S)-lactone 1b. Mp: 146°–148° C.

Other agents for introduction of the BOC group should also be effective. Other solvents such as alcohols, dimethyl formamide (DMF) and dimethylsulfoxide (DMSO) should also work. The presence of a base is necessary to scavenge the acid formed. A weak base is preferred.

CHART A

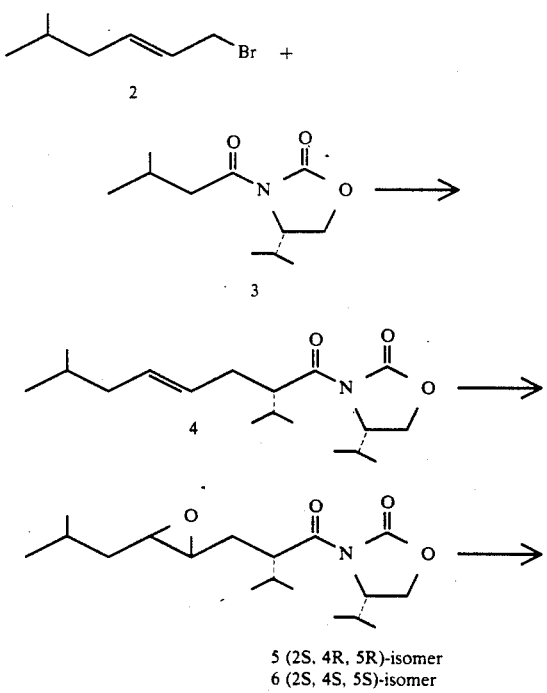

5 (2S, 4R, 5R)-isomer
6 (2S, 4S, 5S)-isomer

-continued
CHART A
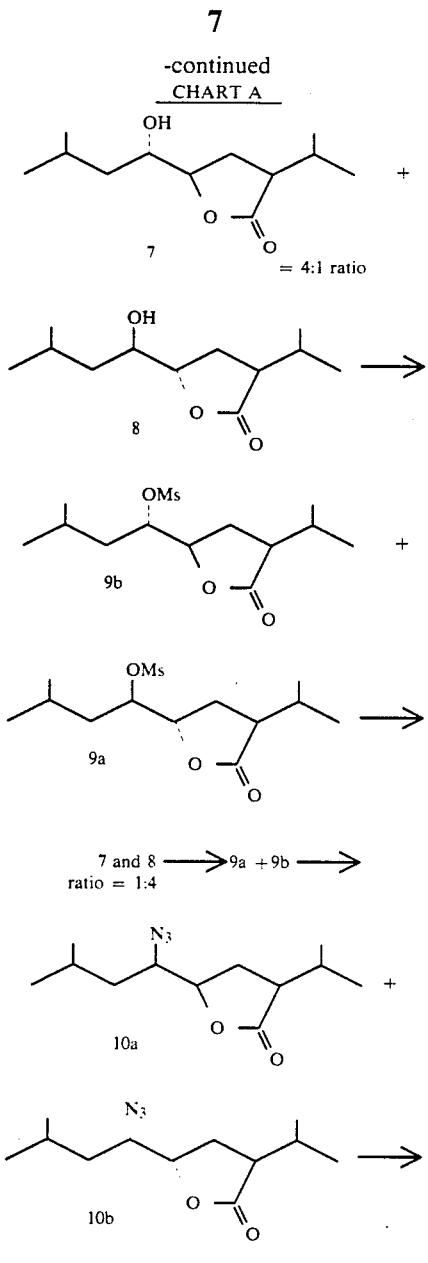
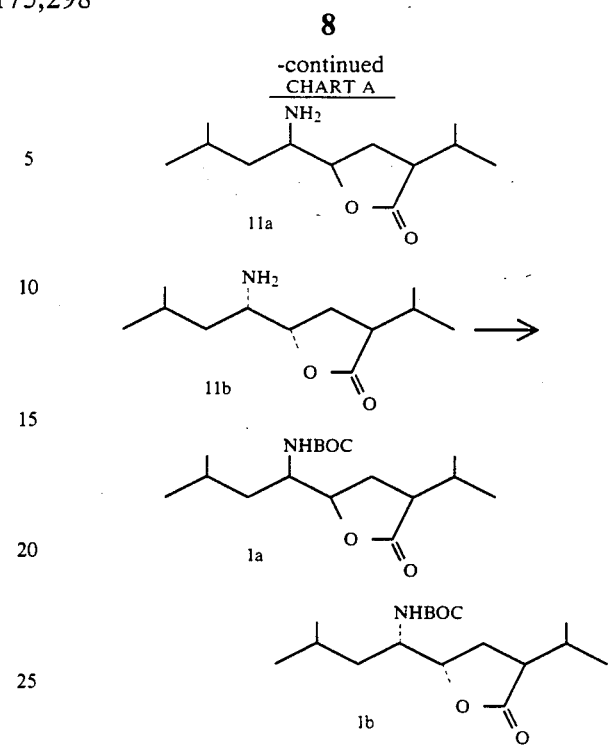
I claim:
1. A compound selected from the compounds depicted below:
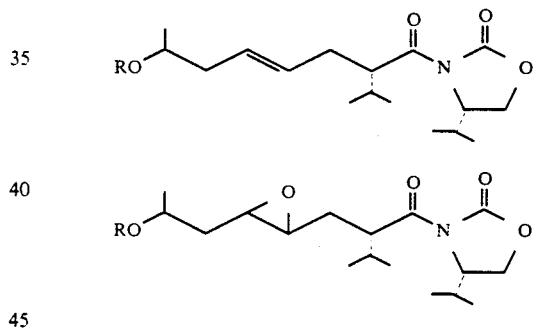
wherein R is benzyl or tert-butyl.
* * * * *